US012629492B2

(12) United States Patent
    Succetti

(10) Patent No.: US 12,629,492 B2
(45) Date of Patent: May 19, 2026

(54) CONNECTION COMPONENT FOR A TRACHEAL CANNULA, IN PARTICULAR FOR PROTECTING AGAINST AN UNINTENTIONAL CLOSURE OF SAME

(71) Applicant: Hamilton Medical AG, Bonaduz (CH)

(72) Inventor: Martin Succetti, Scharans (CH)

(73) Assignee: Hamilton Medical AG, Bonaduz (CH)

( * ) Notice: Subject to any disclaimer, the term of this patent is extended or adjusted under 35 U.S.C. 154(b) by 993 days.

(21) Appl. No.: 17/777,869

(22) PCT Filed: Nov. 19, 2020

(86) PCT No.: PCT/EP2020/082693
§ 371 (c)(1),
(2) Date: May 19, 2022

(87) PCT Pub. No.: WO2021/099470
PCT Pub. Date: May 27, 2021

(65) Prior Publication Data
US 2023/0028902 A1      Jan. 26, 2023

(30) Foreign Application Priority Data
Nov. 21, 2019    (DE) ..................... 10 2019 131 549.2

(51) Int. Cl.
  A61M 16/04        (2006.01)
  A61M 16/08        (2006.01)
(52) U.S. Cl.
  CPC .... A61M 16/0816 (2013.01); A61M 16/0463 (2013.01); A61M 16/0833 (2014.02); *A61M 16/0465* (2013.01)
(58) Field of Classification Search
  CPC .......... A61M 16/0816; A61M 16/0833; A61M 16/0463; A61M 16/0465
  See application file for complete search history.

(56) References Cited

U.S. PATENT DOCUMENTS 4,802,474 A      2/1989 Beevers
5,067,496 A    11/1991 Eisele
        (Continued)

FOREIGN PATENT DOCUMENTS

DE        10140292 A1    3/2003
DE      102005030300 B3    7/2006
        (Continued)

OTHER PUBLICATIONS

DE-102015105496-A1 Translation (Year: 2025).*
        (Continued)

*Primary Examiner* — Kendra D Carter
*Assistant Examiner* — Graciela Natalia Lebron De Jesus
(74) *Attorney, Agent, or Firm* — Rankin, Hill & Clark LLP

(57)            ABSTRACT

An attachment for a tracheal cannula that surrounds a cavity and is open in coupling and orifice areas, the attachment having in the coupling area a latching formation for the releasable connection to a mating latching formation of the tracheal cannula, the coupling area surrounding a section of the cavity, the section of the cavity surrounded by the coupling area being centrally penetrated by a virtual coupling axis, the coupling area having a support section, on which the latching formation and a force application area are situated the support section is displaceable between two positions of different radial distance of the latching formation situated on the support section from the coupling axis; the force application area and the latching formation displaceable by an exertion of force on the force application area of the same support section are situated along the coupling axis at an axial distance from each other.

20 Claims, 6 Drawing Sheets

(56)               References Cited

U.S. PATENT DOCUMENTS

|  |  |  |  |  |
|---|---|---|---|---|
| 5,520,174 | A | 5/1996 | Evans et al. | |
| 10,478,287 | B2 | 11/2019 | Fahl | |
| 2004/0177851 | A1 | 9/2004 | Acosta | |
| 2007/0181130 | A1 | 8/2007 | Worley | |
| 2007/0181132 | A1 | 8/2007 | Worley | |
| 2017/0049982 | A1* | 2/2017 | Kavermann | ...... A61M 16/0463 |

FOREIGN PATENT DOCUMENTS

| | | | | |
|---|---|---|---|---|
| DE | 102015105496 A1 * | 10/2016 | ........ | A61M 16/0468 |
| EP | 1479405 A1 | 11/2004 | | |

OTHER PUBLICATIONS

International Preliminary Report on Patentability for corresponding PCT/EP2020/082693 mailed May 17, 2022, 7 pgs.

International Search Report for corresponding PCT/EP2020/082693 mailed Feb. 24, 2021, 16 pgs.

Espacenet Bibliographic data: EP 1479405 (A1), Published Nov. 24, 2004, 1pg.

Espacenet Bibliographic data: DE 10140292 (A1), Published Mar. 6, 2003, 1pg.

Espacenet Bibliographic data: DE 102005030300 (B3), Published Jul. 27, 2006, 1pg.

PrecisionMedical: Trach Guard URL:www.precisionmedical.com/hospital/airway-products/trachguard/c-25/c-105/p-3202 [retrieved on Jul. 10, 2020].

* cited by examiner

CONNECTION COMPONENT FOR A TRACHEAL CANNULA, IN PARTICULAR FOR PROTECTING AGAINST AN UNINTENTIONAL CLOSURE OF SAME

This Application claims priority in PCT application PCT/EP2020/082693 filed on Nov. 19, 2020, which claims priority in German Patent Application DE 10 2019 131 549.2 filed on Nov. 21, 2019, which are incorporated by reference herein.

The present invention relates to an attachment for a tracheal cannula, the attachment surrounding a cavity, the attachment being open or openable both in a coupling area of the attachment as well as in an orifice area of the attachment, differing in location from the coupling area, for providing an access to the cavity, the attachment having in the coupling area a latching formation, which is designed for a form-locking latching engagement with a mating latching formation of the tracheal cannula, the coupling area surrounding a section of the cavity, the section of the cavity surrounded by the coupling area being centrally penetrated by a virtual coupling axis, the coupling axis defining an axial direction along its path, defining a plurality of radial directions orthogonally to its path and defining a circumferential direction running around it, the coupling area having at least one support section, on which at a first location the latching formation is situated and at a second location distinct from the first location a force application area is situated in such a way that by exerting an actuating force on the force application area in the radial direction toward the coupling axis, the support section is displaceable between two positions of different radial distance of the latching formation situated on the support section from the coupling axis.

The present invention further relates to a respiratory assembly, comprising a tracheal cannula or at least a tracheal cannula end piece and such an attachment couplable to the tracheal cannula end piece.

BACKGROUND OF THE INVENTION

An attachment of the kind mentioned at the outset and also a respiratory assembly having such an attachment and a tracheal cannula end piece are known from US 2017/0049982 A1.

The known attachment comprises a coupling area, having slots diametrically opposite one another with respect to the coupling axis and running in the circumferential direction around a subsection of the circumference as latching formations, which are designed for form-locking engagement with corresponding projections on the tracheal cannula end piece. The coupling area forms and end area of the attachment. An end area of the known attachment, which lies opposite in the axial direction with respect to the coupling axis, is closed and designed as a rounded dome.

In an intermediate area between the coupling area and the axially opposite dome-like end area, orifice openings are formed in the circumference of the attachment, again opposite one another with respect to the coupling axis, through which the cavity enclosed by the attachment is accessible.

In the circumferential area between the latching formations of the known attachment, force application areas having slip-resistant ribs are developed on its outer surface, which are intended to facilitate a pressing finger grip between the latching formations in order to achieve a deformation of the coupling area by pressure from the outside on the slip-resistant ribs in the radial direction toward the coupling axis and thus to be able to attach the attachment to the tracheal cannula end piece and to release it from the latter.

In the state in which there is no load acting on it from outside, the coupling area has an oval cross section when viewing a section in a sectional plane that is orthogonal to the coupling axis. In the unloaded state of the attachment, the force application areas are situated in the area of the long semiaxis of the oval cross section, while the latching formations are situated in the area of the short semiaxes. By pressure from outside in the direction toward the coupling axis, the coupling area may be deformed into a shape having a circular cross section and in this state of deformation may be pushed over an essentially cylindrical mating coupling area of the tracheal cannula end piece. If the exertion of the deforming pressure on the force application areas ends, elastic restoring forces press the coupling area back into the original oval cross-sectional shape. They are inhibited in the restoration, however, especially in the area of the short semiaxes, by the mating coupling area overlapping axially with the coupling area, which is in principle a suitable way for developing the connection between the attachment and the tracheal cannula end piece with increased security against unwanted disconnection of the attachment from the end piece.

A further attachment is known from U.S. Pat. No. 5,520,174 A. This known attachment is merely slid with its coupling area onto a mating coupling area of a tracheal cannula and is retained there by frictional engagement.

Attachments related to the present application usually serve to avoid an unwanted closure of a tracheal cannula by parts of the body of the patient wearing the tracheal cannula. Particularly the chin of such a patient may reach the open end of the tracheal cannula and close it in an unfavorable position, so that a flow of respiratory gas through the tracheal cannula would be prevented. This could have fatal consequences for the patient.

Due to this protective function, attachments related to the present application are also known in the respective specialist field as "tracheostomy guard", "tracheotomy guard", "trach guard" or "tracheostomy tube guard".

A disadvantage of the attachment known from US 2017/0049982 A1 is especially its disconnection process, since in the state in which it is mounted on the mating coupling area of the tracheal cannula, a force acting on the force application area deforming the coupling area of the attachment is inhibited by the mating coupling area of the tracheal cannula. Consequently, it may be necessary to exert a very high deforming force, which is difficult to control, however, since the tracheal cannula is inserted in the patient and thus cannot be manipulated arbitrarily. The disconnection process via the tracheal cannula as a force medium may thus entail a unwanted exertion of force on the patient.

SUMMARY OF THE INVENTION

It is therefore the object of the present invention to develop the attachment mentioned at the outset in such a way that it may be connected to a tracheal cannula and disconnected from the latter in a very patient-friendly manner, that is, with the least possible stress on the patient wearing the tracheal cannula.

The present invention achieves this object in an attachment of the species in that the force application area and the latching formation displaceable by the exertion of force on the force application area of the same support section are situated at an axial distance from one another along the coupling axis.

By situating the force application area and the latching formation in a manner that is axially set apart, it is possible according to the present invention, in contrast to the US 2017/0049982 A1 described above, not to deform the entire coupling area by a force exerted radially toward the coupling axis on the force application area, but only the support section. Consequently, due to the axial section from the latching formation, the force application area may be located in an area of the attachment that does not overlap with components of the tracheal cannula in a state in which it is attached to the tracheal cannula as intended. Consequently, the force application area may have force applied to it and be displaced unhindered by components or component sections of the tracheal cannula. A displacement of the latching formation, in particular in order to disengage a form-locking engagement with a mating latching formation of the tracheal cannula, may thus be effected by exerting a lesser force on the force application area than in the related art for two reasons: the component area to be deformed is smaller and a displacement of the force application area is not impeded or rendered difficult by the tracheal cannula even in the coupled state. A lesser force is easier to control and apply with precision, which is why the risk of a reactive force onto the patient is lower than in the related art.

The cavity enclosed by the attachment is preferably a continuous cavity, so that the cavity connects the coupling area with the orifice area. The cavity thus preferably forms a flow channel between the coupling area and the orifice area along which respiratory gas is able to flow between the coupling area and the orifice area. For hygienic reasons, one of the areas or both areas may be closed by closure means prior to coupling to a tracheal cannula. These closure means, however, are removable from the respective area so that a coupling opening exists in the coupling area and an orifice opening exists in the orifice area, through which the cavity enclosed by the attachment is accessible from the external surroundings of the attachment.

In order to be able to use the greatest possible portion of the force exerted on the force application area in the radial direction toward the coupling axis for a displacement of the latching formation situated on the same support section as the force application area, it is advantageous if the force application area and the latching formation of the same support section are situated at least in sections in the same circumferential area in the circumferential direction around the coupling axis. Even more preferably, the force application area and the latching formation are situated entirely in the same circumferential area, so that there is only an axial distance, but no circumferential distance, between the force application area and the latching formation of the same support section.

For clarification, a force application area and a latching formation are situated in sections in the same circumferential area if the force application area extends beyond the latching formation in a first circumferential direction and the latching formation extends beyond the force application area in a second circumferential direction opposite to the first circumferential direction. If one component section of the force application area or the latching formation extends beyond the respective other in both opposite circumferential directions, because the one has a greater circumferential extension than the other, or only in one circumferential direction, without the other extending beyond the one in the opposite circumferential direction, or if no component section extends beyond the respective other, because they have the same circumferential extension, then the force application area and the latching formation are situated entirely in the same circumferential area.

In a preferred structural development, the support section may comprise a support arm connected to the main component body so as to be movable relative to the latter. By exerting the actuation force, the support arm may be tiltable with respect to the main component body about a tilting axis that is skewed with respect to the coupling axis, so as thereby to effect the displacement of the form-locking formation by approach to the and/or by displacement away from the coupling axis. "Skewed" in this instance means at a distance from the coupling axis and non-parallel to it. For a particularly effective displacement of the latching formation toward the coupling axis and away from it, the extension direction of the tilting axis together with the extension direction of the coupling axis preferably encloses an angle in the range of 70° to 110°. Since the distance between the force application area and the latching formation runs axially, that is, along the coupling axis, the tilting axis together with the coupling axis preferably encloses a right angle.

The support section may be developed as a single-arm lever, in which case the force application area and the latching formation are situated on the same side of the tilting axis on the same support section, so that a radial actuation displacement of the force application area effects a displacement of the latching formation of the same support section in the same direction, but of different magnitude. A quantitatively lesser displacement of the force application area radially toward the coupling axis is thus able to effect a quantitatively greater displacement of the latching formation located at an axial distance away from the force application area. To this end, the force application area may be located closer to the tilting axis than the latching formation associated by being situated on the same support section. The support section then transforms the actuation displacement into a quantitatively greater effective displacement.

As an alternative to the previously mentioned approach, the support section may be designed as a dual-arm lever, one lever respectively extending in a different, preferably diametrically opposite, direction from the tilting axis. In this case, the force application area and the latching formation are situated on different sides of the tilting axis on the same support section, so that a radial actuation displacement of the force application area effects an oppositely directed effective displacement of the latching formation of the same support section.

Irrespective of a single-arm or dual-arm design, the at least one support section is preferably developed on the attachment in such a way that the force application area is actuated only in one direction, that is, radially toward the coupling axis and thereby effects a displacement of the latching formation. After the termination of an exertion of force on the force application area, the latching formation may be restored by restoring means provided on the attachment, including the material elasticity of the component sections involved in the displacement of the support section. The actuation of the force application area preferably serves to release a form-locking engagement between the latching formation and the mating latching formation, not the establishment of such a form-locking engagement. The form-locking engagement may be permanently ensured by the restoring means described above, which counteract a displacement of the latching formation out of its form-locking engagement. The establishment of a form-locking latching engagement of the latching formation and the mating latching formation may occur automatically by the preload effect of the restoring means.

The above-described design approach of the support section as a single-arm lever thus makes it possible that a latching engagement of the latching formation with the mating latching formation is a form-locking engagement, in which the support section and/or the latching formation are/is situated, relative to the coupling axis, radially within the mating coupling area and/or the mating latching formation of the tracheal cannula.

If it is desired that, following the establishment of a latching engagement between the attachment and the tracheal cannula, the supporting section and/or the latching formation are/is located outside of the mating coupling area and/or the mating latching formation of the tracheal cannula, then this may be achieved by the design approach of the support section as a dual-arm lever described above.

In principle, it is conceivable to situate the support arm on the main component body so as to be movable around the tilting axis via a separate axle component. Additionally, a spring component may be provided as preload and/or restoring means, in order to preload the support arm in a predetermined position, from which it may be deflected by the application of force on the force application area described above. Such a design approach built from multiple components is complex, however. Due to the resulting lower number of components it is therefore preferred that the support arm is connected in one piece with the main component body, so that a displacement of the latching formation is brought about by deformation of at least one section of the attachment. In this case, the tilting axis may be a bending axis and/or torsion axis formed by material of the support arm and of the main component body. The tilting axis will be predominantly or completely a bending axis in the aforementioned case of the design of the support section as a single-arm lever, whose support arm is connected in one piece with the main component body. The tilting axis will be predominantly or completely a torsion axis in the aforementioned case of the design of the support section as a dual-arm lever, whose support arm is connected in one piece with the main component body.

The support arm and the main component body may be produced simply and cost-effectively with high precision in its dimensions as a plastic injection-molded part.

By developing the support arm in once piece with the main component body, it is possible, given suitable component dimensions, to utilize the component elasticity for providing a restoring force following the termination of an application of force on the force application areas. The attachment itself is thus its own preload and restoring means. A separate spring component for restoring a latching formation is then not required.

For improving the definition of the position of the attachment when it is connected as intended to a tracheal cannula, the coupling area may include an apron, which surrounds the coupling axis along an angular range. For ensuring the movability of the support section relative to the mentioned apron, the support section may be separated from the apron by at least one groove. When the tracheal cannula is coupled to the attachment as intended, the apron may lie opposite in planar fashion from a corresponding mating apron of the mating coupling area with a small radial gap, so that the radial gap thus formed limits a relative movability of the attachment and the tracheal cannula, especially a tilting motion about a tilting axis orthogonal with respect to the coupling axis. The at least one groove preferably penetrates the attachment completely in the direction of thickness. For ensuring its movability toward the coupling axis and away from it, the support section may be situated at least in an area between two grooves containing the latching formation, the grooves preferably both penetrating the attachment completely in the direction of thickness.

A groove may also be developed in sections around the force application area, which again preferably penetrates the attachment completely in the direction of thickness, in order to reduce the resistance of the attachment against a displacement of the force application area toward the coupling axis and/or away from the coupling axis. For the same purpose, the area of the attachment surrounding the force application area may be developed having a lesser material thickness than the force application area.

The attachment preferably has more than one support section, preferably exactly two support sections. The two support sections are situated preferably diametrically opposite one another with respect to the coupling axis or are at least situated in circumferential sectors diametrically opposite one another having respectively an angular extension between 20° and 75°. This allows for the advantageous one-handed operation of the attachment in particular when disconnecting from the tracheal cannula, since it is possible to bring the force application areas of essentially diametrically opposite support sections closer to each other using two fingers of one hand, which is at the same time a radial approach of each of these force application areas to the coupling axis. The approach of a force application area of a support section to the coupling axis brings about a radial displacement of the latching formation of the same support section.

The apron preferably has two apron sections, between which the at least one support section is situated in the circumferential direction. By dividing the apron into two apron sections, an apron may be provided having a certain deformability, which facilitates connecting the attachment to the tracheal cannula. Additionally or alternatively, the coupling area may comprise the aforementioned preferred two support section having each one latching formation, respectively at least one apron section being situated between the support sections in the circumferential direction. Thus it is possible to combine the advantage of the one-handed operation with the advantage of an increased positional definition of the attachment on the tracheal cannula.

In order to be able to provide on the one hand a particularly secure connection of the attachment to the tracheal cannula and on the other to prevent injuries to the patient by the attachment coupled to his tracheal cannula, the coupling area, according to a preferred development of the present invention, may have a first, more rigid material, and the attachment may have a second, less rigid material at its section situated closer to the orifice area. Its elastic modulus is used to assess the rigidity of a material.

Such an attachment comprising two different materials may also be produced by injection molding, namely, by two-component injection molding. The attachment then comprises a main component body made up of two parts: a first main component body part is made of the more rigid material and a second main component body part, preferably integrally connected to the first, is made of the less rigid material. The support arm is then preferably formed in one piece with the first main component body part.

Furthermore, the risk of injury of the patient by the attachment may be reduced by avoiding corners and edges on the outer surface of the attachment. For this purpose, the attachment may be developed between the coupling area and the orifice area as a tube or hood curved around an axis of curvature that is orthogonal to the coupling axis. The orifice area may then be connected to the patient's tracheal cannula in a manner that points away from the head of the patient, so that an edgeless rounded section of the attachment faces the patient, in particular the patient's chin area.

In order to ensure that the attachment likewise is not closed in unwanted fashion by a part of the body of the patient, as is feared in the case of the tracheal cannula, the attachment may have in the orifice area a greater orifice opening and a smaller auxiliary opening situated at a distance from the orifice area. Even in the event of a faulty positioning of the attachment on a tracheal cannula and in the event that main parts of the patient rest against the attachment, at least one of the openings of the orifice opening and the auxiliary opening remains open. Preferably, the orifice opening and the auxiliary opening are therefore situated in diametrically opposite circumferential sections relative to the coupling axis. Particularly preferably, the orifice opening and the auxiliary opening are situated diametrically opposite from each other relative to the coupling axis.

A respiratory assembly is considered below, which comprises a tracheal cannula or at least a tracheal cannula end piece and an attachment couplable to the tracheal cannula or the tracheal cannula end piece, as is described and developed above. Embodiments of the attachment and of the tracheal cannula indicated above in the connected state are further developments of this respiratory assembly. For connecting the attachment to the tracheal cannula, only the tracheal cannula end piece is important, which includes the mating coupling area required for the connection to the attachment. In the description of an attachment, connected as intended to a tracheal cannula, and only such an intended connection state is described above, the tracheal cannula always includes a tracheal cannula end piece having a mating coupling area.

The tracheal cannula end piece therefore has a mating coupling area extending along a virtual connection axis, which includes the mating latching formation for the form-locking latching engagement with the latching formation of the attachment. The mating coupling area surrounds a cannula cavity virtually centrally penetrated by the connection axis. In the state of the attachment and the tracheal cannula end piece, in which these are connected as intended, the coupling axis and the connection axis are collinear or parallel.

The mating latching formation may encircle the connection axis completely in the circumferential direction, but preferably extends in the circumferential direction around the connection axis only over a circumferential section of the mating coupling area, while a further circumferential section is not designed for the latching engagement with the latching formation. This makes it possible to limit the number of possible relative positions and thus the number of possible disadvantageous relative alignments of the attachment and the tracheal cannula end piece. At the location where a circumferential section is not designed for latching engagement with the latching formation, the attachment is unable to latch in a manner noticeable for the operating service person, so that a possible misalignment or at least disadvantageous alignment of the attachment relative to the tracheal cannula end piece can already be corrected when coupling the attachment to the tracheal cannula. The mentioned relative position is normally a rotary relative position of the attachment relative to the tracheal cannula end piece in the circumferential direction around the coupling axis or connection axis.

The tracheal end piece preferably has a tube section extending along the connection axis, at the one longitudinal end of which the mating coupling area is preferably developed. The tracheal cannula end piece may further have a connection formation projecting from the tube section, which is designed for the flow-conducting connection to a respiratory gas line. Thus, it is possible to connect the preferably developed tracheal cannula end piece both to the attachment as well as to a respiratory gas line. The connection to the respiratory gas line makes it possible to supply respiratory gas to the patient in the required volume.

To prevent, in the most secure way possible, an unwanted closure of the orifice opening of the attachment in the state in which it is connected as intended to the tracheal cannula end piece, the latching formation and the mating latching formation may be situated and/or developed on the respective components in such a way that an orifice opening in the orifice area of the attachment is situated in the same circumferential section as the connection formation. For a respiratory gas line is normally introduced to the tracheal cannula end piece from a direction in which as little interaction as possible with a part of the body of the patient wearing the tracheal cannula is to be expected. This expected small extent of interaction with the patient is also advantageous for positioning the orifice opening, so that the latter advantageously opens in the same circumferential area, from which respiratory gas is supplied to the patient.

The posture of a ventilated patient is not always static, nor is the posture of the patient always defined from the start. It is therefore advantageous to position the attachment on the tracheal cannula end piece with a certain adjustment play, in order to be able to respond to an unexpected or altered posture of the patient. Since for the purpose of providing a functioning protection of the tracheal cannula against closure with the aid of the attachment, it is essentially the circumferential direction into which its orifice opening points that is most critical, in the operational state in which it is latched as intended on the tracheal cannula end piece, the attachment may be designed to be swivable around the connection axis relative to the tracheal cannula end piece in a swivel range that is smaller than the entire circumference. This may be achieved in that a latching projection of the latching formation and the mating latching formation in the circumferential direction is designed to be shorter than the latching recess cooperating with the projection for producing a form-locking latched connection.

As was already explained at the outset, for a permanently secure connection of the attachment and the tracheal cannula, it is advantageous if the attachment and the tracheal cannula end piece overlap along an overlap area in the operational state in which they are latched to each other as intended. In particular, the coupling area and the mating coupling area may overlap along the then collinear or parallel axes of coupling axis and connection axis. The force required for actuating the force application area may then be kept low if the force application area is situated outside of the overlapping area.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1B:
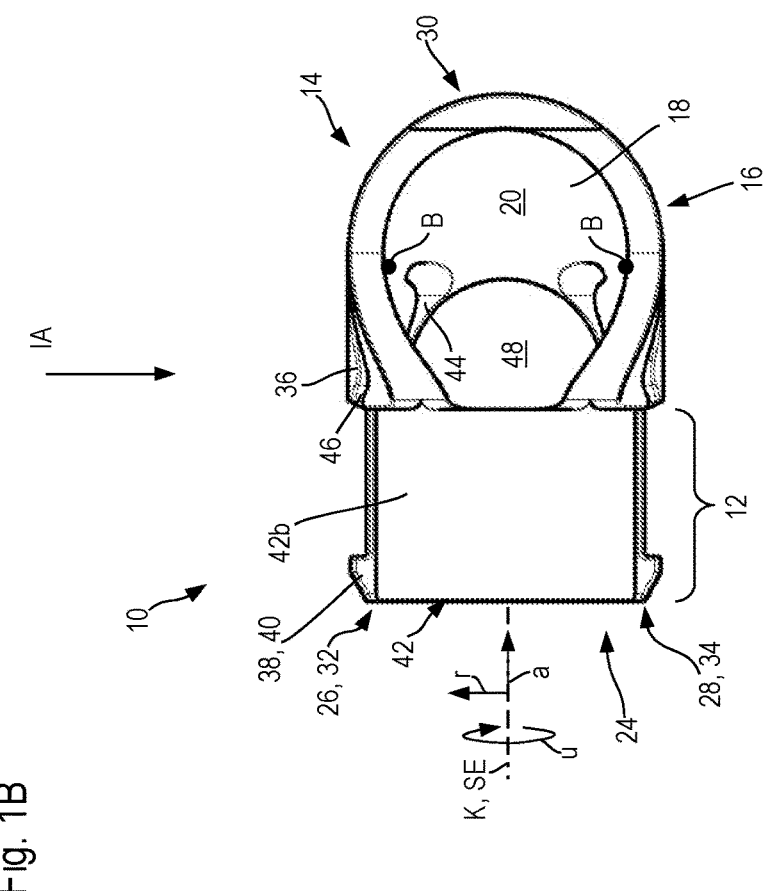
FIG. 1A a lateral view of a first specific embodiment of an attachment according to the invention having a single-arm support arm, FIG. 1B a bottom view of the attachment from FIG. 1A, when viewed from the direction of arrow IB in FIG. 1A, FIG. 2A a top view of the attachment from FIG. 1A, when viewed from the direction of arrow IIB in FIG. 1A, FIG. 2B a rear view of the attachment from FIG. 3A, when viewed from the direction of arrow IIB in FIG. 1A, FIG. 3A a lateral view of a second specific embodiment of an attachment according to the invention having a dual-arm support arm, FIG. 3B a rear view of the attachment from FIG. 3A, when viewed from the direction of arrow IIIB in FIG. 3A, FIG. 4A a lateral view of a third specific embodiment of an attachment according to the invention having a dual-arm support arm and including materials of different rigidities, which are used in different areas of the attachment, FIG. 4B a top view of the attachment from FIG. 4A, when viewed from the direction of arrow IVB in FIG. 4A, FIG. 5A a lateral view of a first specific embodiment of a respiratory assembly, comprising a first specific embodiment of a tracheal cannula end piece and further comprising the attachment of the first specific embodiment of FIGS. 1A through 2B, FIG. 5B a bottom view of the respiratory assembly from FIG. 5A, when viewed from the direction of arrow VB in FIG. 5A, FIG. 6A a lateral view of a second specific embodiment of a respiratory assembly according to the invention, comprising a second specific embodiment of a tracheal cannula end piece and further comprising the attachment of the second specific embodiment of FIGS. 3A and 3B, and FIG. 6B a lateral view only of the second specific embodiment of the tracheal cannula end piece from FIG. 6A, without the attachment coupled thereto.

Referring now to the drawings wherein the showings are for the purpose of illustrating preferred and alternative embodiments of the invention only and not for the purpose of limiting the same, in FIGS. 1A through 2B, a first specific embodiment of an attachment according to the invention is generally labeled by reference numeral 10. In FIGS. 1B through 2B, arrows IA indicate the direction of view of FIG. 1A onto the attachment 10. Attachment 10 has a coupling area 12 extending along a coupling axis K, which is connected in one piece with a hood section 14. Hood section 14 has an orifice area 16 of an orifice opening 18 (see FIGS. 1B and 2B).

Coupling axis K defines an axial direction a along its extension direction, radial directions r orthogonally to its extension direction, and a circumferential direction u encircling it.

Orifice opening 18 opens in the radial direction away from coupling axis K.

Attachment 10 surrounds a cavity 20, which is accessible from outside attachment 10 both from the orifice opening 18 as well as from a coupling opening 22 (see FIG. 2B), which is developed on a free coupling end 24 of the coupling area 12 facing away from hood section 14.

Figure 1A:
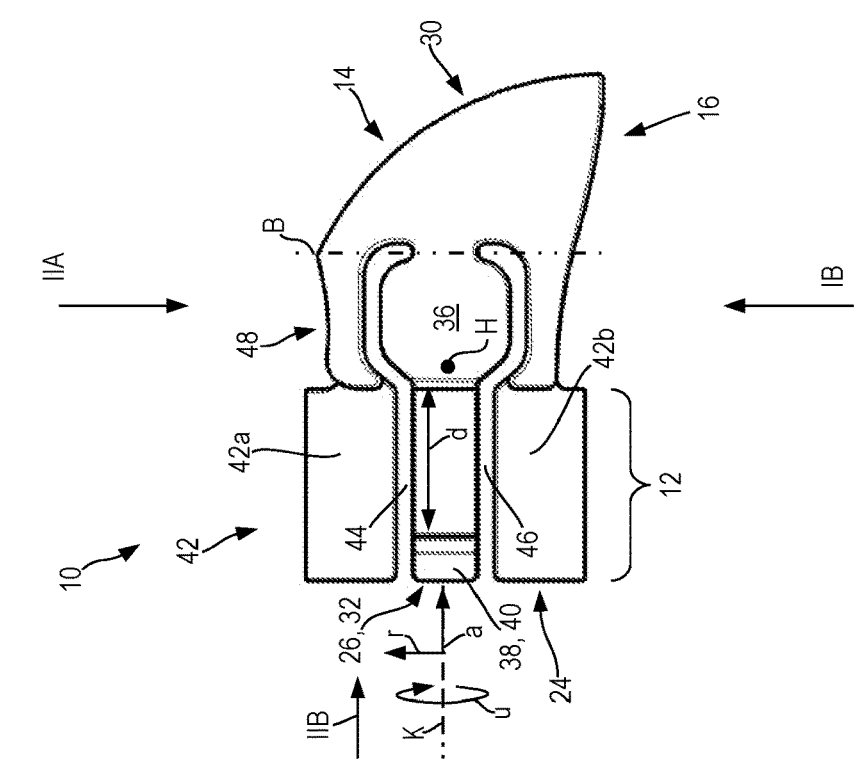
Figure 2B:
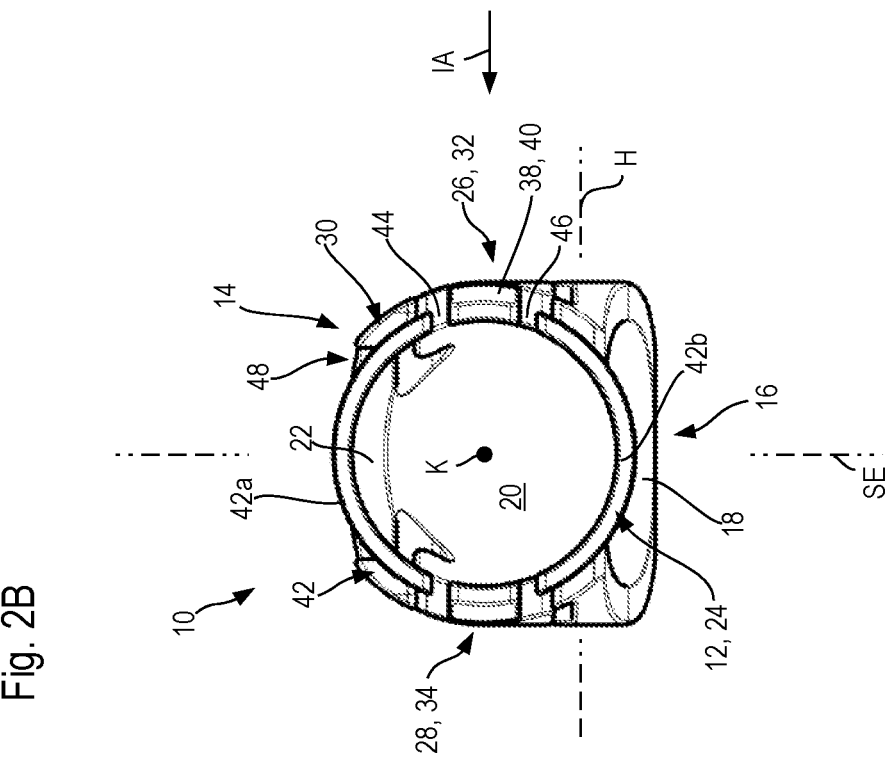
Figure 2A:
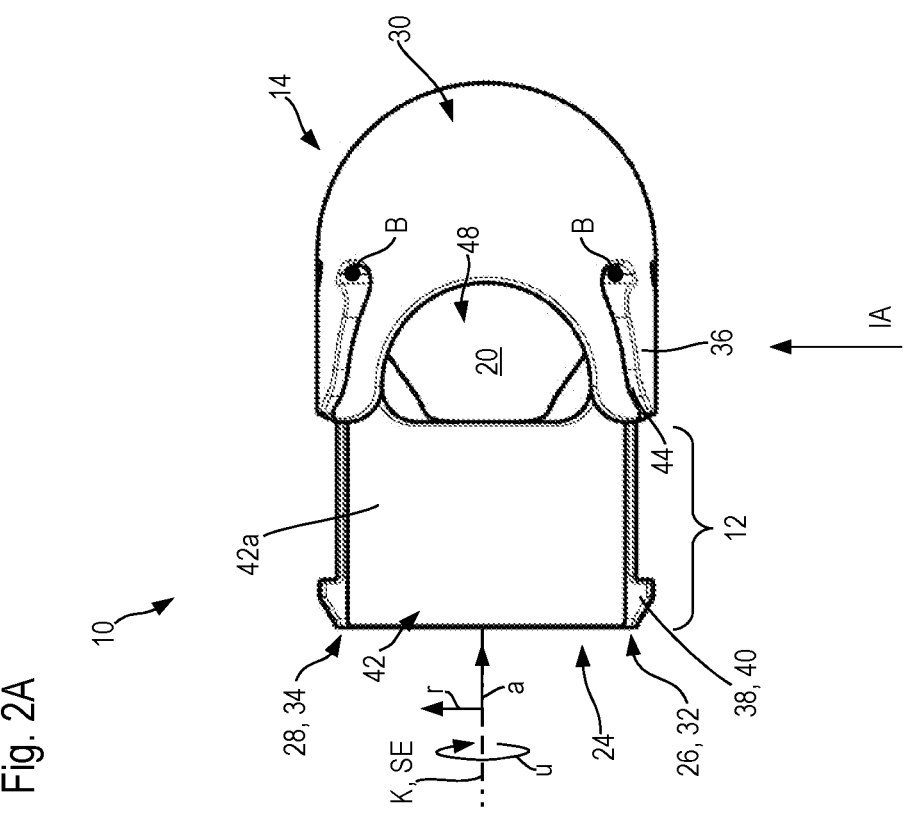

While starting from coupling opening 22, coupling area 12 forms an essentially cylindrical and/or conical flow channel section along coupling axis K, hood section 14 forms a flow channel section curved around an axis of curvature H, which is orthogonal to coupling axis K and to the drawing plane of FIG. 1A, connecting to the linear flow channel section of coupling area 12 and leading to orifice opening 18.

Attachment 10 comprises two support sections 26 and 28, which are developed as support arms 32 and 34 projecting on one side from a main component body 30. Since attachment 10 of the first specific embodiment is preferably designed in mirror symmetry with respect to a mirror symmetry plane SE containing coupling axis K, which is parallel to the drawing plane of FIG. 1A and orthogonal to the drawing planes of FIGS. 1B, 2A and 2B, it suffices to describe below only the support section 26 or the support arm 32 in detail. The description provided for support section 26 and thus for support arm 32 also applies under the aforementioned symmetry condition also to the respectively other support section 28 or support arm 34.

The support section 26 developed as support arm 32 is developed in one piece with the main component body 30 and is bendable relative to the main component body 30 around a bending axis B running preferably orthogonally to coupling axis K and at a distance from the latter. In order to be able to bring this bending about, a force application area 36 is developed on a section of support arm 32 situated closer to bending axis B, on which, by hand or finger application from outside the attachment, an actuating force is exertable, which runs radially with respect to coupling axis K and acts in the direction of coupling axis K. The force application area 36 is part of coupling area 12.

At the axial distance d, but without circumferential distance from force application area 36, a latching formation 38 in the form of a latching projection 40 protruding radially away from coupling axis K is developed in one piece with support arm 32 and thus with the force application area 36. By exerting the actuating force described previously on force application area 36, the latching formation 38 may be displaced against the material elasticity of support arm 32 and of the main component body 30 by bending deformation around the bending axis B toward coupling axis K. Latching formation 38 may thereby be removed from an existing form-locking latching engagement with a mating latching formation of a tracheal cannula or of a tracheal cannula end piece, in order to disconnect the attachment 10 from the tracheal cannula end piece.

The coupling area 12 has an apron 42 having two apron sections 42a and 42b, which are situated in the circumferential direction u around coupling axis K in such a way that in circumferential direction u an apron section is followed by a support section or a support arm and vice versa. In the operational state situated as intended on a tracheal cannula end piece, apron sections 42a and 42b are situated radially within a mating coupling area of the tracheal cannula end piece and across from the latter with a tight radial gap. The outer surfaces of apron sections 42a and 42b are preferably developed partially cylindrically or partially conically with coupling axis K as cylinder or cone axis, in order to be able to ensure a certain relative rotatability of attachment 10 relative to the tracheal cannula end piece in the state coupled as intended to the end piece.

In order to ensure the bending deformabililty of support section 26 or of support arm 32, the latter is separated in sections from main component body 30 by grooves 44 and 46 in the circumferential direction on both sides of support section 26.

Hood section 14 is developed in dome-like fashion as a curved shell in order to avoid risk of injury of a patient coming into contact with hood section 14, for example by rubbing and the like. For this reason, the force application areas (see force application area 36) situated in the area of hood section 14 are also formed having convexly curved surface, as seen from outside, which across groves 44 and 46 in circumferential direction u forms an uninterrupted continuation of the surface of the rest of hood section 14. The hood section 14 and the force application areas 36 have no corners or edges on their outer surface. The width of grooves 44 and 46 is so small that groove edges cannot have an irritating effect on the skin of a patient who comes into contact with hood section 14. Incidentally, the groove edges may be rounded off.

Diametrically opposite the orifice opening 18, an auxiliary opening 48 is formed in the attachment 10, which however has a smaller opening area than orifice opening 18 due to the hood-like design of hood section 14 between coupling area 12 and orifice area 16. Due to the formation of the auxiliary opening 48, however, respiratory gas is still able to flow between the auxiliary opening 48 and the coupling opening 22 even when the orifice opening 18 is covered or closed in unwanted fashion. Since the auxiliary opening 48 is situated diametrically opposite the orifice opening 18 with respect to coupling axis K, it is highly improbable that both openings 18 and 48 are simultaneously closed by unforeseen events.

In the present exemplary embodiment, the cavity 20 surrounded by attachment 10 connects the openings 18, 22 and 48 in such a way that each of these openings is able to communicate with every other in fluidic fashion.

A second specific embodiment of an attachment 110 according to the invention will now be described in connection with FIGS. 3A and 3B. Identical and functionally identical components and component sections as in the first specific embodiment are provided with the same reference numerals in the second specific embodiment, but increased by 100. The second specific embodiment will be described in the following only to the extent as it differs from the first specific embodiment of FIGS. 1A through 2B, to the description of which express reference is otherwise made also for the explanation of the second specific embodiment. The arrow IIIA in FIG. 3B indicates the direction from which attachment 110 is viewed in FIG. 3A.

The essential difference of the second specific embodiment with respect to the first specific embodiment lies in the fact that the support sections 126 and 128 in the form of support arms 132 and 134 are developed, not as single-arm levers, but as dual-arm levers. Again, with reference to the mirror symmetry already described above, only support section 126 will be described below in place of both support sections 126 and 128.

The support section 126 or the support arm 132 is connected in one piece to main component body 130 in an area between the force application area 136 and the latching formation 138 in the circumferential direction u. As a result, the grooves 144 and 146 running from the coupling end 124 axially into the coupling area 112 are axially shorter than the corresponding grooves 44 and 46 of the first specific embodiment, which run right through to the connection location of the force application area 36 and the main component body 30. Due to the connection of the support section 126 to the main component body 130 between the force application area 136 and the latching formation 138, a further groove 145 may be developed around the force application area 136 in order to facilitate the displacing actuation of the force application area 136.

As an alternative to the development of the further groove 145, the force application area 136 may cohere without groove and without interruption with the rest of the main component body 130. A displacing actuation of the force application area 136 may then be facilitated in that an area of the main component body 130 surrounding the force application area 136 is developed having a lesser material thickness than the force application area 136, so that the area surrounding the force application area may be deformed by a lesser force than the force application area 136 or that it deforms to a greater degree than the force application area given a specified force acting from outside toward the coupling axis. Consequently, the surrounding area contiguous with the force application area opposes a displacement of the force application area 136 radially inward toward the coupling axis K only with a negligible resistance.

Quite fundamentally, but especially in the case in which the force application area is not readily differentiable from the surrounding component area, perhaps because no groove 145 exists, it is advantageous if a haptically perceptible formation is provided on the force application area, which makes it possible to sense the location of the force application area by touch. In that case, the force application area may be found even in darkness or in case of a highly soiled attachment. Such a formation is for example the U-shaped projection 147, which is situated on the force application area 136 on the outer side of attachment 110 facing away from coupling axis K. The radially outwardly protruding projection 147 is preferably formed in one piece with the force application area 136, for example by injection molding.

Further preferably, the projection 147 is a projection 147 indicating a direction along the coupling axis, as in the present example a U-shaped projection 147, the free limb ends preferably pointing along the coupling axis K to the respective latching formation 138 provided with the force application area 136 on the same support section or pointing in the coupled state to the coupled tracheal cannula end piece. In place of the illustrated U-shaped design, another protrusion design may be chosen. For example, a triangle, an arrow, a V-shaped, a T-shaped or an E-shaped design may be chosen as the direction-indicating protrusion design.

In contrast to the first specific embodiment, in which the support section 26 is connected in the axial direction a in one piece with the main component body 30, so that the force application area 36 and the latching formation 38 are situated on one and the same side of the bending axis B, the force application area 136 and the latching formation 138 in the second specific embodiment are situated on different sides of the connection of the support section 126 to the main component body 130.

As a consequence, when exerting a force on the force application area 136 in the direction toward the coupling axis K, the connection of the support section 126 to the main component body is strained not by bending, as in the first specific embodiment, but by torsion. When displacing the force application area 136 toward coupling axis K, the connection of the support section 126 rotates against its material and component elasticity around the torsion axis T, whereby the latching formation 138 is indeed again displaced simultaneously with the force application area 136 relative to the coupling axis K, but in the opposite direction to the displacement of the force application area 136. The displacements of the force application area 36 and of the latching formation 38 of the first specific embodiment by contrast occur in the same direction, i.e., either both mentioned component sections 36 and 38 approach coupling axis K simultaneously or both simultaneously withdraw from it.

Due to the displaceability of the force application area 136 and the latching formation 138 in opposite directions, the coupling area 112 of the second specific embodiment is designed to surround a mating coupling area of a tracheal cannula or a tracheal cannula end piece radially on the outside. By displacing the force application area 136 toward the coupling axis K or into cavity 120, the latching formation 138 is displaced away from coupling axis K and may thus be displaced for example out of a latching recess on the outer circumference of a mating coupling area.

A third specific embodiment of an attachment 210 will now be described in connection with FIGS. 4A and 4B. Components and component sections identical and functionally identical to those in the first and/or second specific embodiment are labeled in the third specific embodiment with the same reference numerals, but for differentiation in the number range from 200 to 299. The third specific embodiment is described below only to the extent that it differs from the first and the second specific embodiments of FIGS. 1A through 3B, to the description of which express reference is otherwise made also for explaining the third specific embodiment. The arrow IVA in FIG. 4B indicates the direction from which the attachment 110 is viewed in FIG. 3A.

The third specific embodiment of attachment 210 corresponds in its function to the second specific embodiment of attachment 110, i.e., the support sections 226 and 228 are developed as dual-arm levers, which rotate around a torsion axis T situated between the force application area 236 and the latching formation 238. To this extent, with respect to establishing and releasing a form-locking engagement with a mating latching formation, the third specific embodiment functions like the second specific embodiment 110.

The bending axes B and torsion axes T shown in the figures are tilting axes in the sense of the above introduction of the description.

The third specific embodiment 210 is produced from two different materials, preferably in a two-component injection molding process. The main component body 230 therefore has two main component body parts 230a and 230b.

The first main component body part 230a is made of a more rigid material and essentially comprises the coupling area 212. The support sections 226 and 228 are made entirely of the same more rigid material as the first main component body part 230a and are formed in one piece with the latter.

The second main component body part 230b is made of a less rigid material, for example a thermoplastic elastomer, and comprises essentially the hood section 214. Due to the use of the less rigid material in the hood section 214, hood section 214 yields more readily by deformation to an external load than the more rigid first main component body part 230a, so that the hood section 214 does not cause irritations or injuries even in more frequent skin contact with the patient. In clinical use, the hood section 114 may normally be reachable by the chin area of the patient.

To improve the connection of the first and second main component body parts 230a and 230b, no groove is preferably formed between the edge of the force application area 236 and the second main component body part 230b. Instead, the second main component body part 230b is injection molded directly onto force application area 236. Due to the lower elastic modulus of the material of the second main component body part 230b, injection molding this part 230b onto the force application area 236 does not impair the movability of the force application area 236. By injection molding the second main component body part 230b, the force required for displacing the force application area 236 toward the coupling axis K is increased only negligibly in comparison to the second specific embodiment.

Figure 5B:
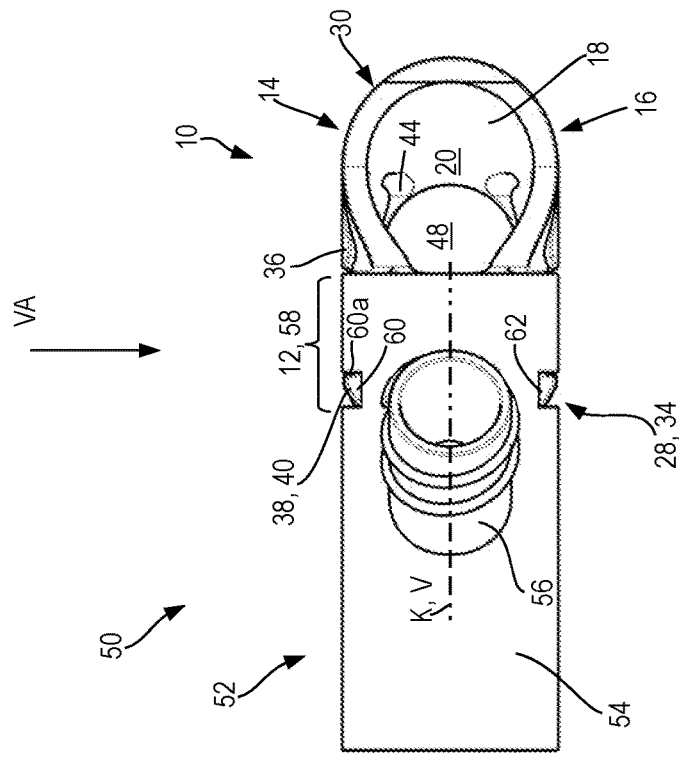
Figure 5A:
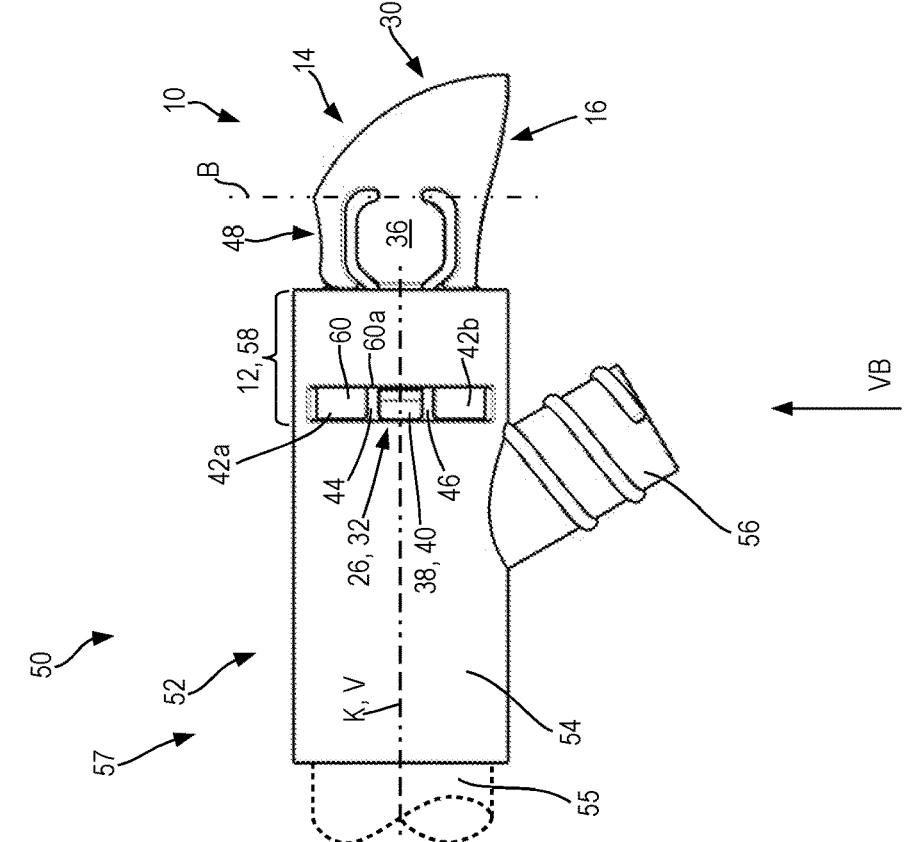

FIGS. 5A and 5B show a first specific embodiment of a respiratory assembly 50 according to the invention. FIG. 5A shows the respiratory assembly 50 from the side, while FIG. 5B shows it from below. The viewing direction of FIG. 5A is indicated in FIG. 5B by the arrow VA.

Respiratory assembly 50 comprises an attachment 10 according to FIGS. 1A through 2B, which is coupled, as intended, with a tracheal cannula end piece 52. The tracheal cannula end piece 52 comprises a tube section 54, which in the illustrated example has an essentially cylindrical shape, running in any event preferably linearly along the imaginary extended coupling axis K. At its longitudinal end far from attachment 10, tracheal cannula end piece 52 is connected or connectible in a manner known per se to a tracheal cannula channel 55, indicated only by dashed lines, so as to form a tracheal cannula 57.

At its bottom side, a connection fitting 56 protrudes from tube section 54, which is designed for connecting to a respiratory gas line that is not shown. As a connection formation for the connection to a respiratory gas line, the connection fitting 56 makes it possible to supply respiratory gas, if required, to a patient via the tracheal cannula 57.

The attachment is preferably coupled to the tracheal cannula end piece 52 in such a way that the orifice opening 18 points in the direction, in which the connection fitting 56 protrudes from tube section 54. Since in clinical application the connection fitting 56 is normally situated pointing away from the head of the patient wearing the tracheal cannula 57, the orifice opening 18 of the attachment coupled to the tracheal cannula end piece 52 as shown in FIG. 5A likewise points away from the head of the patient, so that the orifice opening 18 is not reachable by the patient even in the case of a very unfavorable posture and is thus protected against closure.

The longitudinal end of tube section 54 nearest to the attachment 10 is developed as a mating coupling area 58. The mating coupling area 58 and the coupling area 12 overlap when attachment 10 is coupled as intended to tracheal cannula end piece 52. The previously described apron sections 42a and 42b are situated opposite to inner surfaces of the mating coupling area 58 with a tight radial gap in between. The distance d is dimensioned so that the force application area 36 does not overlap with the mating coupling area 58. It is therefore not hindered in its operability by the mating coupling area 58.

The mating coupling area 58 extends along a connection axis V, which in the illustrated normal coupling state is collinear with the coupling axis K of the coupling area 12 of attachment 10.

In two diametrically opposite circumferential sections with respect to connection axis V, the mating coupling area 58 comprises in each case a latching recess 60 and 62 fully penetrating the tube section 54 in the direction of thickness as mating latching formations. The latching projection 40 of the support section 26 or support arm 32 engages into latching recess 60 in form-locking fashion, and the latching projection of support section 28 or support arm 34 engages into the latching recess 62. The apron sections 42a and 42b as well as the end areas of the support arms cover the latching recess 60 and largely close it.

The latching projection 40 engages in a latching manner behind an edge 60*a* of the latching recess 60 situated closer to attachment 10 and thus prevents attachment 10 from being pulled out of tracheal cannula end piece 52. An extraction is nevertheless possible if the force application areas 36 of the support sections 26 and 28 are displaced toward coupling axis K to such an extent that the latching formation 38 of support section 26 and the latching formation of support section 28 are disengaged from the engaged edges of the latching recesses 60 and 62, respectively.

The latching recesses 60 and 62 respectively run in the circumferential direction u around coupling axis K or connection axis V only over a predetermined angular range. Along their circumferential extension, the latching recesses 60 and 62 allow for a relative movement, more precisely a relative rotation of the attachment 10 relative to tube section 54 around coupling axis K. This makes it possible to adjust the attachment 10 and in particular the orifice opening 18 within the predefined limits to a given situation.

Figure 3B:
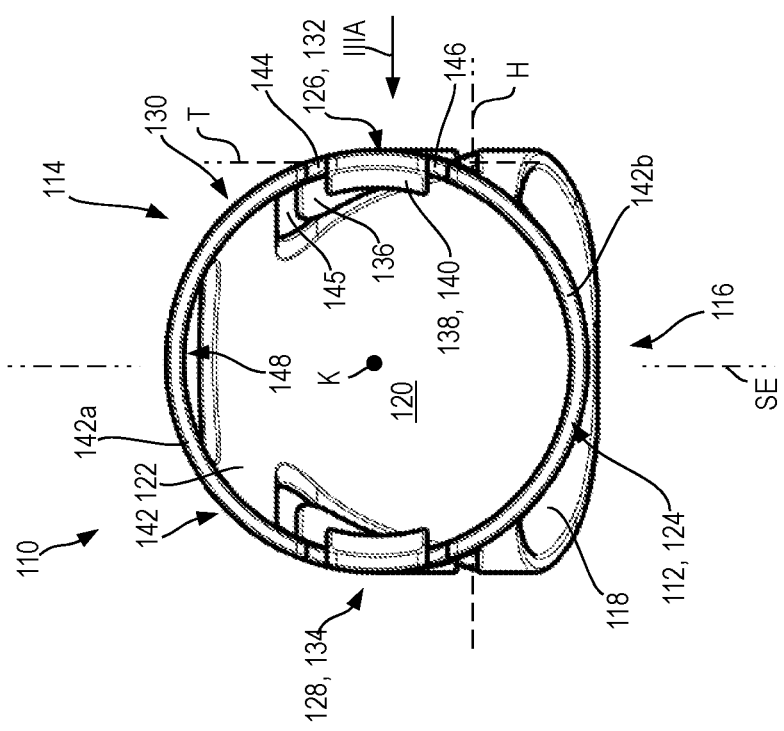
Figure 3A:
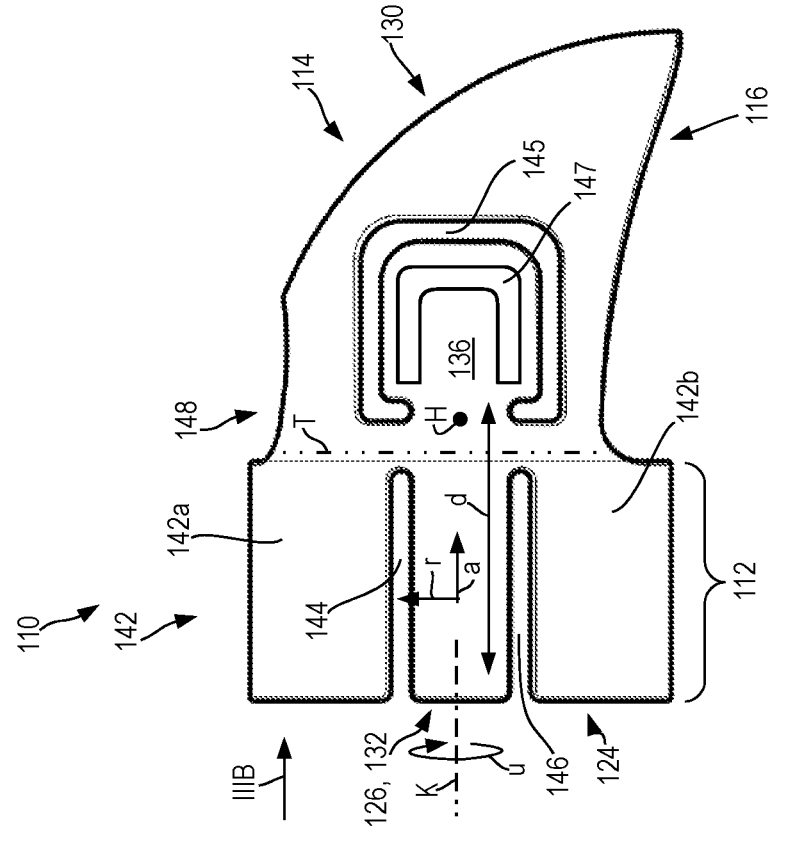
Figure 4B:
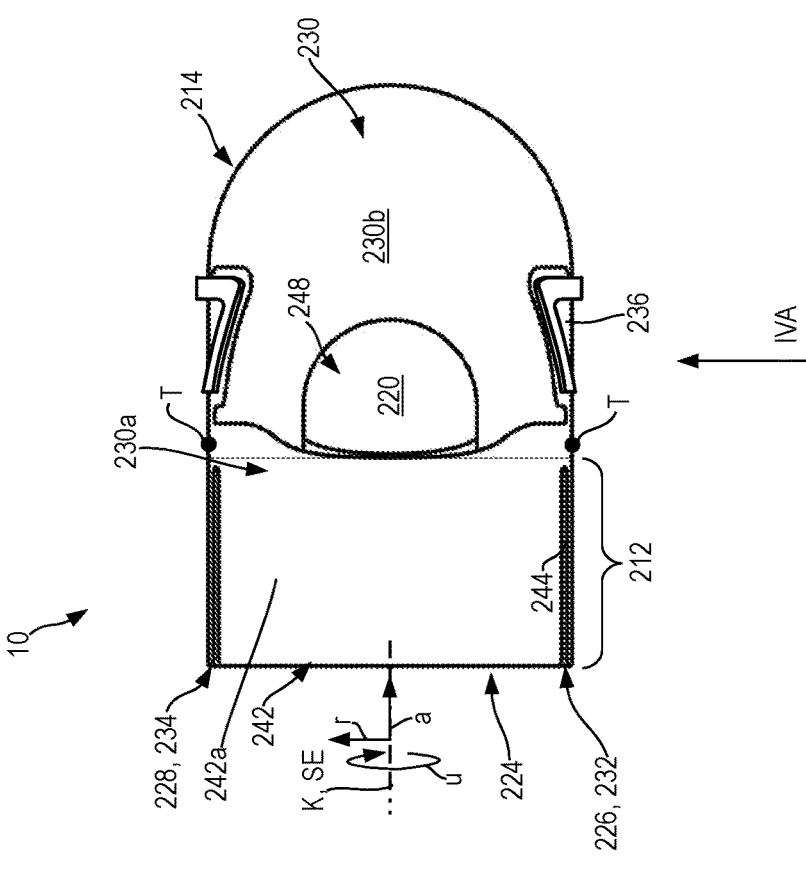
Figure 4A:
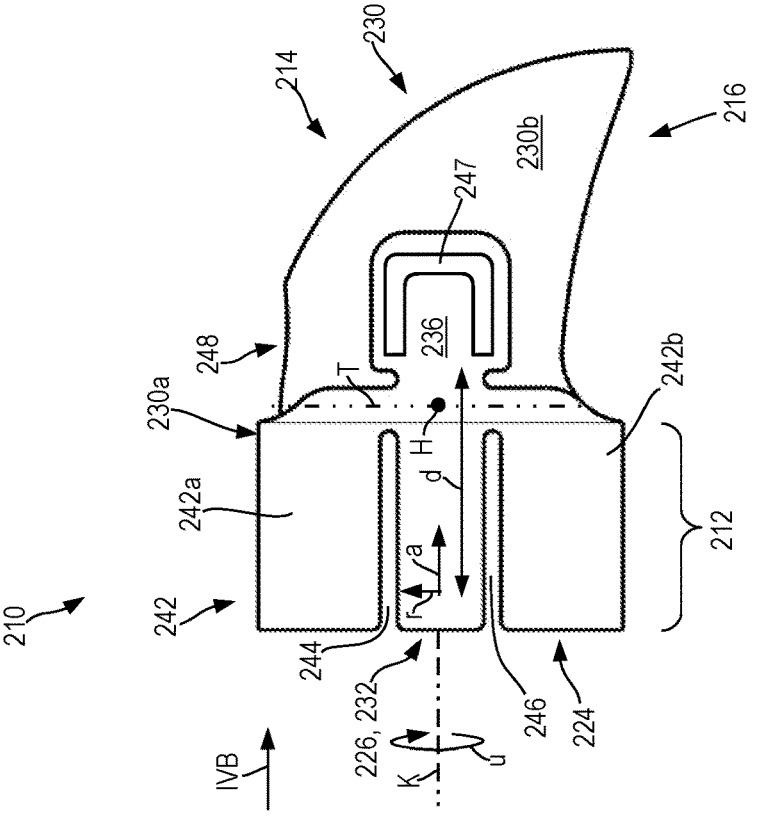
Figure 6B:
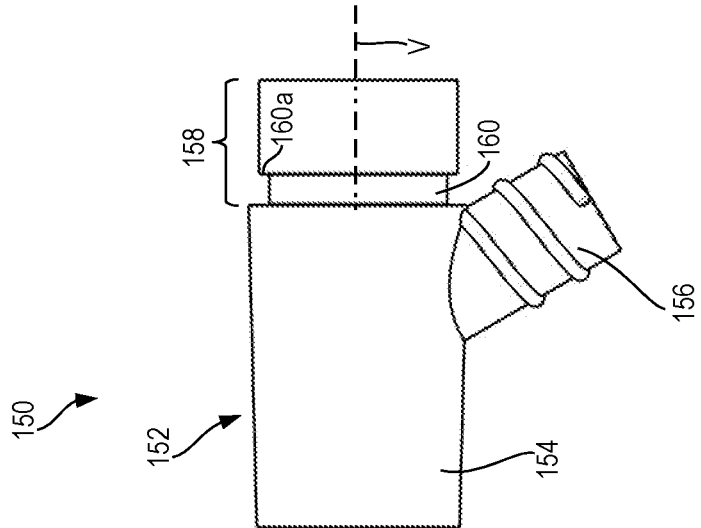
Figure 6A:
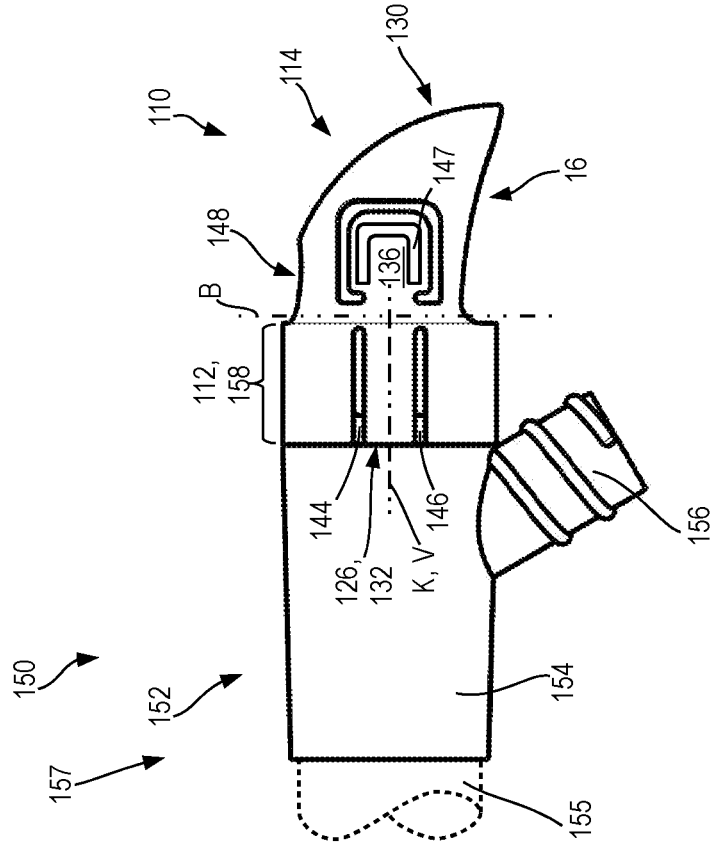

FIG. 6A shows a second specific embodiment of a respiratory assembly 150 according to the invention, which shows a second specific embodiment of a tracheal cannula end piece 152 and coupled to it in intended fashion the second specific embodiment of the attachment 110 of FIGS. 3A and 3B.

Identical and functionally identical components and component sections as in the first specific embodiment of the respiratory assembly 50 of FIGS. 5A and 5B are provided with the same reference numerals in the second specific embodiment of FIG. 6A, but increased by 100. The second specific embodiment of respiratory assembly 150 will be described in the following only to the extent as it differs from the first specific embodiment, to the description of which reference is otherwise made also for the explanation of the second specific embodiment.

The essentially sole functional difference between the second and the first specific embodiments of the respiratory assembly is the fact that the attachment 110 with its coupling area 112 radially surrounds on the outside the mating coupling area 158 of the tracheal cannula end piece 152 with respect to the collinear axes of coupling axis K and connection axis V.

The latching formations of the support sections 126 and 128, that is, for example the latching projection 140, consequently do not engage into a mating latching formation of the mating coupling area 158 radially from the inside radially to the outside, but rather in the opposite direction radially from the outside radially to the inside.

The mating latching formation of the tracheal cannula end piece 152 is developed as a completely encircling groove 160, but may also be developed in the circumferential direction only in sections on tube section 154. Groove 160 does not penetrate through tube section 154 in the direction of thickness.

Since in the coupled state, the coupling area 112 covers the mating coupling area 158 in FIG. 6A when viewed radially from the outside, the tracheal cannula end piece 152 from FIG. 6A is shown in FIG. 6B separately without attachment 110. The figure shows the circumferential groove 160 as the latching recess and its edge 160*a* engaged from behind by the latching formations of the support sections 126 and 128, edge 160*a* having a smaller diameter than the outer surface of the rest of the tube section beyond groove 160. Due to the smaller diameter of the mating coupling area 158, compared to the rest of the tube section, the attachment 110 in the coupled state is able to form an essentially stepless, flush outer surface along the common axis of coupling axis K and connection axis V across essentially the entire outer surface of the respiratory assembly 150 with the exception of the hood section 114 and the connection fitting 156.

In place of attachment 110, it is also possible for attachment 210 to be coupled to the tracheal cannula end piece 152.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. An attachment for a tracheal cannula, the attachment surrounding a cavity, the attachment being open or openable both in a coupling area of the attachment as well as in an orifice area of the attachment, differing in location from the coupling area, for providing an access to the cavity, the attachment having in the coupling area a latching formation, which is designed for a releasable connection to a mating latching formation of the tracheal cannula, the coupling area surrounding a section of the cavity, the section of the cavity surrounded by the coupling area being centrally penetrated by a virtual coupling axis, the virtual coupling axis defining an axial direction along its path, defining a plurality of radial directions orthogonally to its path and defining a circumferential direction running around it, the coupling area having at least one support section, on which at a first location the latching formation is situated and at a second location distinct from the first location a force application area is situated in such a way that by exerting an actuating force on the force application area in the radial direction toward the virtual coupling axis, the at least one support section is displaceable between two positions of different radial distance of the latching formation situated on the at least one support section from the virtual coupling axis, wherein the force application area and the latching formation displaceable by an exertion of force on the force application area of a same one of the at least one support section are situated along the virtual coupling axis at an axial distance from each other, wherein the attachment is developed between the coupling area and the orifice area as a tube or a hood curved around an axis of curvature that is orthogonal to the virtual coupling axis.

2. The attachment as recited in claim 1, wherein the force application area and the latching formation of the same one of the at least one support section are situated in the circumferential direction around the virtual coupling axis at least in sections in the same circumferential area.

3. The attachment as recited in claim 2, wherein the at least one support section comprises a support arm connected to a main component body in a manner that is movable relative to the latter, which, by exerting the actuating force, is tiltable around a tilting axis that is skewed with respect to the virtual coupling axis, an extension direction of the tilting axis together with an extension direction of the virtual coupling axis enclosing an angle in the range of 70° to 110°.

4. The attachment as recited in claim 1, wherein at least one support section comprises a support arm connected to a main component body in a manner that is movable relative to the latter, which, by exerting the actuating force, is tiltable around a tilting axis that is skewed with respect to the virtual coupling axis, an extension direction of the tilting axis together with an extension direction of the virtual coupling axis enclosing an angle in the range of 70° to 110°.

5. The attachment as recited in claim 4, wherein the support arm is connected in one piece with the main component body, so that a displacement of the latching formation is effected by deformation of at least one section of the attachment, the tilting axis being a bending axis and/or a torsion axis.

6. The attachment as recited in claim 4, wherein the force application area and the latching formation are situated on a same side of the tilting axis on the same one of the at least one support section, so that a radial actuation displacement of the force application area effects an effective displacement of the latching formation of the same one of the at least one support section in a same direction, but of different magnitude.

7. The attachment as recited in claim 6, wherein the force application area is situated closer to the tilting axis than the associated latching formation, so that the at least one support section transforms the actuation displacement into an effective displacement that is greater in terms of magnitude.

8. The attachment as recited in claim 1, wherein the coupling area includes an apron, which surrounds the virtual coupling axis along an angular range, the at least one support section being separated from the apron by a groove.

9. The attachment as recited in claim 8, wherein the apron has two apron sections, between which in the circumferential direction, the at least one support section is situated, and/or the coupling area includes two of the at least one support sections having each one latching formation, between which in the circumferential direction respectively at least one apron section is situated.

10. The attachment as recited in claim 1, wherein the coupling area comprises a first, more rigid material and the attachment comprises in its section closer to the orifice area a second, less rigid material.

11. The attachment as recited in claim 1, wherein the attachment has at the orifice area a greater orifice opening in terms of area and a smaller auxiliary opening in terms of area that is remote from the orifice area.

12. A respiratory assembly, comprising a tracheal cannula end piece and the attachment couplable to the latter as recited in claim 1, wherein the tracheal cannula end piece has a mating coupling area extending along a connection axis including the mating latching formation for a form-locking engagement with the latching formation of the attachment, the mating coupling area surrounding a cannula cavity centrally virtually penetrated by the connection axis, the mating latching formation extending in the circumferential direction around the connection axis only over a circumferential section of the mating coupling area, while a further circumferential section is not designed for the latching engagement with the mating latching formation.

13. The respiratory assembly as recited in claim 12, wherein the attachment is developed between the coupling area and the orifice area as a tube or a hood curved around an axis of curvature that is orthogonal to the virtual coupling axis, the tracheal cannula end piece includes a tube section extending along the connection axis and a connection formation protruding from the tube section, which is developed for a flow-conducting connection to a respiratory gas line, the latching formation and the mating latching formation being situated and/or developed on the respective components in such a way that an orifice opening in the orifice area of the attachment is situated in an operational state latched on the tracheal cannula end piece in the same circumferential section as the connection formation.

14. The respiratory assembly as recited in claim 13, wherein the attachment, in the operational state latched on the tracheal cannula end piece, is swivable relative to the tracheal cannula end piece around the connection axis in a swivel range that is smaller than the entire circumference.

15. The respiratory assembly as recited in claim 14, wherein the attachment and the tracheal cannula end piece overlap in a mutually latched operational state along an overlap area, the force application area being situated outside of the overlap area.

16. The respiratory assembly as recited in claim 12, wherein the attachment, in an operational state latched on the tracheal cannula end piece, is swivable relative to the tracheal cannula end piece around the connection axis in a swivel range that is smaller than the entire circumference.

17. The respiratory assembly as recited in claim 12, wherein the attachment and the tracheal cannula end piece overlap in a mutually latched operational state along an overlap area, the force application area being situated outside of the overlap area.

18. An attachment for a tracheal cannula, the attachment surrounding a cavity, the attachment being open or openable both in a coupling area of the attachment as well as in an orifice area of the attachment, differing in location from the coupling area, for providing an access to the cavity, the attachment having in the coupling area a latching formation, which is designed for a releasable connection to a mating latching formation of the tracheal cannula, the coupling area surrounding a section of the cavity, the section of the cavity surrounded by the coupling area being centrally penetrated by a virtual coupling axis, the virtual coupling axis defining an axial direction along its path, defining a plurality of radial directions orthogonally to its path and defining a circumferential direction running around it, the coupling area having at least one support section, on which at a first location the latching formation is situated and at a second location distinct from the first location a force application area is situated in such a way that by exerting an actuating force on the force application area in the radial direction toward the virtual coupling axis, at least one support section is displaceable between two positions of different radial distance of the latching formation situated on at least one support section from the virtual coupling axis, wherein the force application area and the latching formation displaceable by an exertion of force on the force application area of a same one of the at least one support section are situated along the virtual coupling axis at an axial distance from each other, wherein at least one support section comprises a support arm connected to a main component body in a manner that is movable relative to the latter, which, by exerting the actuating force, is tiltable around a tilting axis that is skewed with respect to the virtual coupling axis, the extension direction of the tilting axis together with the extension direction of the virtual coupling axis enclosing an angle in the range of 70° to 110°, wherein the force application area and the latching formation, are situated on different sides of the tilting axis on the same one of at least one support section, so that a radial actuation displacement of the force application area effects an oppositely directed effective displacement of the latching formation of the same one of the at least one support section.

19. The attachment as recited in claim 18, wherein the support arm is connected in one piece with the main component body, so that a displacement of the latching formation is effected by deformation of at least one section of the attachment, the tilting axis being a bending axis and/or a torsion axis.

20. The attachment as recited in claim 18, wherein the attachment is developed between the coupling area and the orifice area as a tube or a hood curved around an axis of curvature that is orthogonal to the virtual coupling axis.

\* \* \* \* \*